(12) United States Patent
Chen et al.

(10) Patent No.: US 7,749,743 B2
(45) Date of Patent: Jul. 6, 2010

(54) ISOLATED XYLANASE GENE WITH MUTATIONS AND SITE-SPECIFIC MUTAGENESIS METHOD THEREOF

(75) Inventors: Yo-Chia Chen, Neipu Shiang (TW); Hsueh-Ling Cheng, Neipu Shiang (TW); Yu-Chuan Chiang, Puzih (TW)

(73) Assignee: Natiional Pingtung University of Science & Technology, Pingtung County (TW)

( * ) Notice: Subject to any disclaimer, the term of this patent is extended or adjusted under 35 U.S.C. 154(b) by 94 days.

(21) Appl. No.: 11/851,593

(22) Filed: Sep. 7, 2007

(65) Prior Publication Data

US 2008/0254539 A1   Oct. 16, 2008

(30) Foreign Application Priority Data

Apr. 16, 2007   (TW) .............................. 96113280 A (51) Int. Cl.
*C12N 9/24* (2006.01)
(52) U.S. Cl. ..................................................... 435/200
(58) Field of Classification Search ........................ None
See application file for complete search history.

(56) References Cited

OTHER PUBLICATIONS

J. Liu et al. "Direct Cloning of a Xylanse Gene From the Mixed Genomic DNA of Rumen Fungi and Its Expression in Intestinal *Lactobacillus reuteri*", FEMS Micriobiology Letters 251: 233-241 (2005).*
F.W. Paradis et al. "The xynC Gene from Fibrobacter succinogenes S85 Codes for a Xylanase with Two Similar Catalytic Domains". Journal of Bacteriology 175(23): 7666-7672 (Dec. 1993).*

* cited by examiner

*Primary Examiner*—Rebecca E. Prouty
(74) *Attorney, Agent, or Firm*—Alan Kamrath; Kamrath & Associates PA (57) ABSTRACT

An isolated xylanase gene with mutations includes a fifty-eighth amino acid or a thirty-eighth amino acid generated from transforming asparagine to aspartic acid so as to form the isolated xylanase gene. A site-specific mutagenesis method includes: mutating the forty-first amino acid or the thirty-eighth amino acid of the xylanase gene by transforming asparagine to aspartic acid so as to form the isolated xylanase gene.

1 Claim, 5 Drawing Sheets

FIG. 1

```
ATGGCTAGCATGACTGGTGGACAGCAAATGGGTCGGATCCCGTTAACTGTTGCTAAGGCC 60
 M  A  S  M  T  G  G  Q  Q  M  G  R  I  P  L  T  V  A  K  A
CAATGGGGTGGAAACGGTGGTGCCCCTGCTGGTCAAAAATTAAGCGTAGGTGGTGGTCAA 120
 Q  W  G  G  N  G  G  A  P  A  G  Q  K  L  S  V  G  G  G  Q
AACCAACATAAAGGTGTTTTCGATGGCTTCAGTTATGAAATCTGGTTAGATGACACCGGT 180
 N  Q  H  K  G  V  F  D  G  F  S  Y  E  I  W  L  D [D] T  G
GGTAGCGGTTCCATGACCCTTGGTAAAGGTGCAACCTTCAAGGCTGAATGGAGTGCAGCT 240
 G  S  G  S  M  T  L  G  K  G  A  T  F  K  A  E  W  S  A  A
GTTAACCGTGGTAACTTCCTTGCCCGTCGTGGTCTTGACTTCGGTTCTACCAAAAAGGCA 300
 V  N  R  G  N  F  L  A  R  R  G  L  D  F  G  S  T  K  K  A
ACCGATTACGAATACATCGGAATGGATTATGAAGCAAGTTACAGACAAACTGCCAGCGCA 360
 T  D  Y  E  Y  I  G  M  D  Y  E  A  S  Y  R  Q  T  A  S  A
AGTGGTAACTCCCGTCTCTGTGTATACGGCTGGTTCCAAAACCGCGGAGTTCAAGGCGTA 420
 S  G  N  S  R  L  C  V  Y  G  W  F  Q  N  R  G  V  Q  G  V
CCTTTGGTAGAATACTACATCATTGAAGATTGGGTCGACTGGGTACCAGATGCACAAGGA 480
 P  L  V  E  Y  Y  I  I  E  D  W  V  D  W  V  P  D  A  Q  G
AAAATGGTAACCATCGATGGTGCACAATATAAGATTTTCCAAATGGATCACACTGGTCCA 540
 K  M  V  T  I  D  G  A  Q  Y  K  I  F  Q  M  D  H  T  G  P
ACTATCAATGGTGGTAATGAAACCTTTAAGCAATACTTCAGTGTCCGTCAACAAAAGAGA 600
 T  I  N  G  G  N  E  T  F  K  Q  Y  F  S  V  R  Q  Q  K  R
ACTTCTGGTCATATTACTGTATCAGATCACTTTAAGGCATGGGCCAGTCAAGGTTGGGGT 660
 T  S  G  H  I  T  V  S  D  H  F  K  A  W  A  S  Q  G  W  G
ATTGGAAACCTCTATGAAGTTGCATTGAACGCAGAAGGTTGGCAAAGTAGTGGTGTCGCT 720
 I  G  N  L  Y  E  V  A  L  N  A  E  G  W  Q  S  S  G  V  A
GACGTCACCAAGTTGGATGTCTACACCACCAAACAAGGTTCTGCTCCTCGTACTACCACC 780
 D  V  T  K  L  D  V  H  T  T  K  Q  G  S  A  P  R  T  T  T
ACCACTACCCGTACTACTACCCGTACTACTACAAGAACACTTCCAACCACTGGCAATAAG 840
 T  T  T  R  T  T  T  R  T  T  T  R  T  L  P  T  T  G  N  K
TGTTCTGCCAAGATTACTGCCCAAGGTTACAAGTGTTGTAGTGATCCAAATTGTGTTATT 900
 C  S  A  K  I  T  A  Q  G  Y  K  C  C  S  D  P  N  C  V  I
TACTACACTGATGACGATGGTAAATGGGGTAAAGCGGCCGCACTCGAGCACCACCACCAC 960
 Y  Y  T  D  D  D  G  K  W  G  K  A  A  A  L  E  H  H  H  H
CACCACTGA
 H  H
```

```
CAATGGGGTGGAAACGGTGGTGCCCCTGCTGGTCAAAAATTAAGCGTAGGTGGTGGTCAA 60
 Q  W  G  G  N  G  G  A  P  A  G  Q  K  L  S  V  G  G  G  Q
AACCAACATAAAGGTGTTTTCGATGGCTTCAGTTATGAAATCTGGTTAGATGACACCGGT 120
 N  Q  H  K  G  V  F  D  G  F  S  Y  E  I  W  L  D  D  T  G
GGTAGCGGTTCCATGACCCTTGGTAAAGGTGCAACCTTCAAGGCTGAATGGAGTGCAGCT 180
 G  S  G  S  M  T  L  G  K  G  A  T  F  K  A  E  W  S  A  A
GTTAACCGTGGTAACTTCCTTGCCCGTCGTGGTCTTGACTTCGGTTCTACCAAAAAGGCA 240
 V  N  R  G  N  F  L  A  R  R  G  L  D  F  G  S  T  K  K  A
ACCGATTACGAATACATCGGAATGGATTATGAAGCAAGTTACAGACAAACTGCCAGCGCA 300
 T  D  Y  E  Y  I  G  M  D  Y  E  A  S  Y  R  Q  T  A  S  A
AGTGGTAACTCCCGTCTCTGTGTATACGGCTGGTTCCAAAACCGCGGAGTTCAAGGCGTA 360
 S  G  N  S  R  L  C  V  Y  G  W  F  Q  N  R  G  V  Q  G  V
CCTTTGGTAGAATACTACATCATTGAAGATTGGGTCGACTGGGTACCAGATGCACAAGGA 420
 P  L  V  E  Y  Y  I  I  E  D  W  V  D  W  V  P  D  A  Q  G
AAAATGGTAACCATCGATGGTGCACAATATAAGATTTTCCAAATGGATCACACTGGTCCA 480
 K  M  V  T  I  D  G  A  Q  Y  K  I  F  Q  M  D  H  T  G  P
ACTATCAATGGTGGTAATGAAACCTTTAAGCAATACTTCAGTGTCCGTCAACAAAAGAGA 540
 T  I  N  G  G  N  E  T  F  K  Q  Y  F  S  V  R  Q  Q  K  R
```

FIG. 5

ISOLATED XYLANASE GENE WITH MUTATIONS AND SITE-SPECIFIC MUTAGENESIS METHOD THEREOF

BACKGROUND OF THE INVENTION

1. Field of the Invention

The present invention relates to an isolated xylanase gene with mutations and a site-specific mutagenesis method thereof. More particularly, the present invention relates to the site-specific mutagenesis method utilized to mutate a fifty-eighth amino acid or a thirty-eighth amino acid of a xylanase gene from asparagine to aspartic acid so as to form the xylanase gene with mutations.

2. Description of the Related Art

Generally, most xylans widely exist in structural polysaccharides of plants. The xylan can naturally function as a protective material for celluloses of plants such that the protective material can be a limitation in processing the natural material of plants. For example, in manufacturing pulps of paper materials, there is a need of using a chloride material as a bleaching agent to bleach the pulp due to the fact that the xylan and lignin adhere to surfaces of the celluloses of the plants. After processing the bleaching procedure, the reacted chloride may produce residual products of chemicals which are toxic and carcinogenic substances. The toxic and carcinogenic substances are persistent and bioaccumulating in the natural environment. This seriously destroys the natural environment and the ecological system.

In the livestock industry, animal feed is widely fed and delivered to the animal digestive system. The animal feed naturally contains celluloses and hemicelluloses of plants with which to cover its valuable nutrients. The celluloses and hemicelluloses of plants separate the valuable nutrients from enzyme existing in the animal digestive system. In this manner, the valuable nutrients of the animal feed cannot be reacted with the enzyme or cannot be absorbed by animal intestines of the digestive system. Accordingly, this affects the growth of animals. If the undigested nutrients are excreted from the animal digestive system, there are pollution sources of the undigested nutrients which cause environmental pollution. Hence, there is a need for removal of the xylan from the celluloses and hemicelluloses of plants.

Generally, there is a conventional xylanase which is separated from a rumen microorganism and can be widely used to eliminate the above problem due to the fact that the xylanase can decompose the xylan. In the papermaking industry, the xylanases can decompose the hemicelluloses existing in the paper pulp such as links between the lignin and the celluloses and between the lignin and the hemicelluloses. Accordingly, the lignin can be released from the paper pulp in the bleaching process. In the food-processing industry, an oligosaccharide is used not only to discompose the hemicelluloses in fruit juices but also to be raw materials of foods. In the livestock industry, the oligosaccharide is added to the animal feed. In this manner, the xylanases of the oligosaccharide can be utilized to decompose the xylan in attempting to aid absorption of the valuable nutrients by animal intestines of the digestive system. Accordingly, this results in an increase of the absorbed amount of the valuable nutrients.

The primary problem occurring during use of the conventional xylanases is due to the fact that the xylanases possess a lower degree of reaction activity. Hence, there is a need of a greater amount of use for higher reaction activity which results in an increase of material cost. In addition to this, the conventional site-specific mutagenesis method cannot enhance the reaction activity of the xylanase.

It is a common practice that a mutation method is utilized to improve a characteristic of enzymes in the art. A conventional mutation method is disclosed in the book by Joshi et al. entitled "Hydrogen Bonding and Catalysis": "a novel explanation for how a single amino acid substitution can change the pH optimum of a glycosidase," J. Mol. Biol. (2000) 299, 255-279. A thirty-fifth amino acid of a xylanase gene of *bacillus circulans* is mutated from asparagine to aspartic acid for reducing a pKa value of the *bacillus circulans* so as to enhance its acid-resistibility. However, this conventional mutation method cannot effectively enhance the reaction activity of the xylanase gene.

As is described in greater detail below, the present invention provides an isolated xylanase gene with mutations and a site-specific mutagenesis method thereof. The site-specific mutagenesis method is processed to mutate a fifty-eighth amino acid or a thirty-eighth amino acid of a xylanase gene from asparagine to aspartic acid so as to form the xylanase gene with the mutations in such a way as to mitigate and overcome the above problem. Advantageously, the isolated xylanase gene of the present invention is successful in increasing its reaction activity and reducing material cost.

SUMMARY OF THE INVENTION

The primary objective of this invention is to provide an isolated xylanase gene with mutations. The xylanase gene with mutations is generated from mutating a fifty-eighth amino acid or a thirty-eighth amino acid of a xylanase gene from asparagine to aspartic acid which can increase reaction activity of the xylanase gene.

The secondary objective of this invention is to provide a site-specific mutagenesis method for increasing the reaction activity of xylanases. The site-specific mutagenesis method is processed to mutate at least one amino acid of an enzyme gene from asparagine to aspartic acid so as to form a mutated gene of the enzyme. Accordingly, the site-specific mutagenesis method is achieved in increasing its reaction activity of the enzyme.

The isolated xylanase gene in accordance with an aspect of the present invention includes a fifty-eighth amino acid or a thirty-eighth amino acid of the xylanase gene being mutated by transforming asparagine to aspartic acid so as to form the isolated xylanase gene.

In a separate aspect of the present invention, the site-specific mutagenesis method includes the step of mutating the fifty-eighth amino acid or the thirty-eighth amino acid of the xylanase gene by transforming asparagine to aspartic acid so as to form the isolated xylanase gene.

Further scope of the applicability of the present invention will become apparent from the detailed description given hereinafter. However, it should be understood that the detailed description and specific examples, while indicating preferred embodiments of the invention, are given by way of illustration only, since various variations will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not imitative of the present invention, and wherein:

FIG. 2 is a schematic view illustrating a nucleotide sequence (SEQ ID NO:3) of an isolated xylanase gene with mutations in accordance with a first embodiment of the present invention;

DETAILED DESCRIPTION OF THE INVENTION

Figure 1:
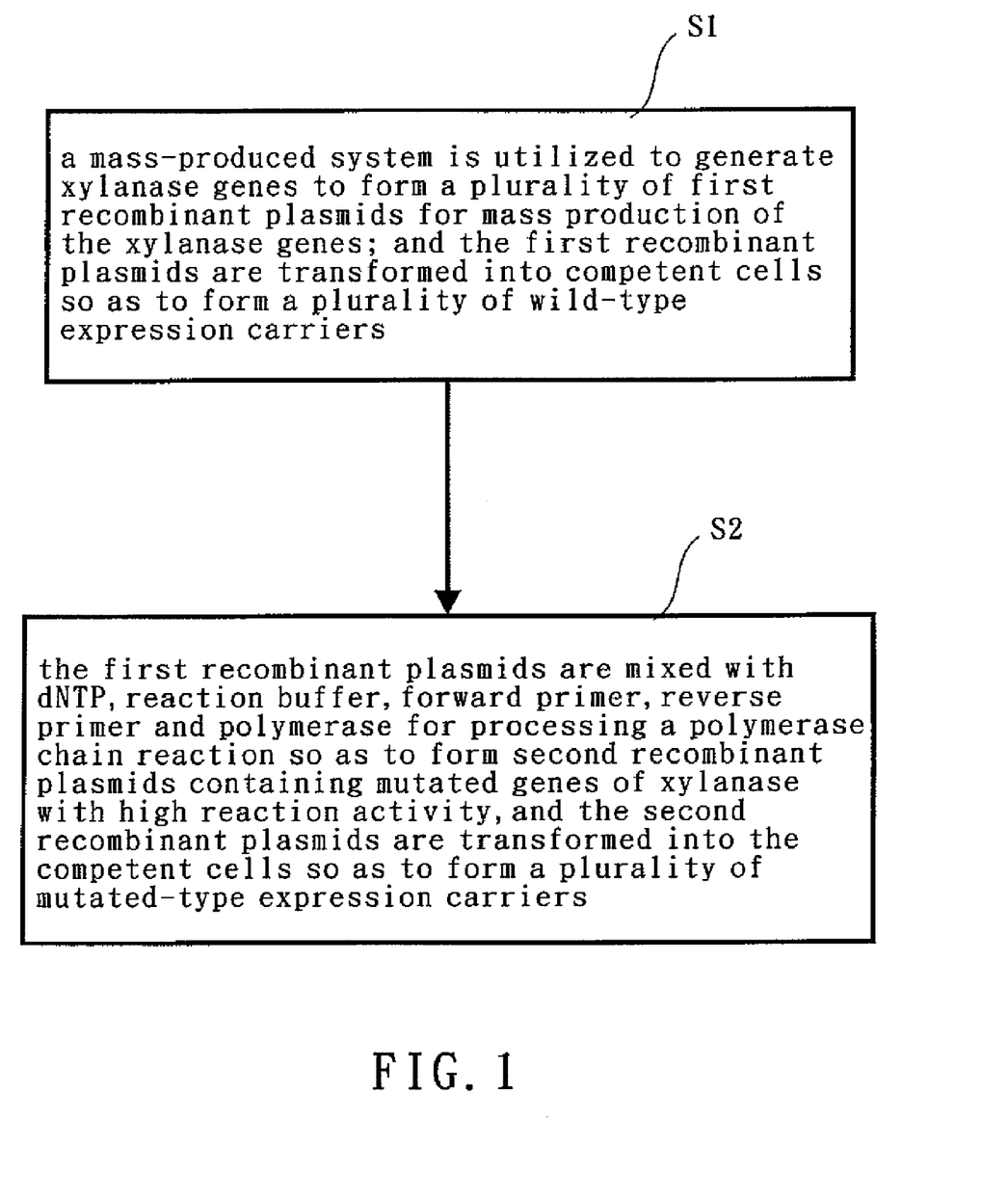
FIG. 1 is a flow chart illustrating a site-specific mutagenesis method for an isolated xylanase gene with mutations in accordance with a preferred embodiment of the present invention.

Turning now to FIG. 1, a flow chart of a site-specific mutagenesis method for an isolated xylanase gene with mutations in accordance with the preferred embodiment of the present invention is illustrated. The site-specific mutagenesis method of the preferred embodiment of the present invention includes the steps of utilizing carriers to generate a plurality of xylanase genes which is designated as step "S1"; and executing a polymerase chain reaction which is designated as step "S2". In step "S1", the carriers are utilized to generate the xylanase genes to form a plurality of first recombinant plasmids for mass production of the xylanase genes; and the first recombinant plasmids are transformed into competent cells so as to form a plurality of wild-type expression carriers. In step "S2", the first recombinant plasmids are mixed with dNTP, reaction buffer, forward primer, reverse primer and polymerase for processing the polymerase chain reaction so as to form second recombinant plasmids, and the second recombinant plasmids are transformed into the competent cells so as to form a plurality of mutated-type expression carriers. Since the polymerase chain reaction can reproduce a great number of the xylanase genes and each of the forward primer and the reverse primer has a mutation position, the reproduction of the xylanase genes in the polymerase chain reaction can generate the isolated xylanase gene with mutations. In this manner, a fifty-eighth amino of the xylanase gene is mutated from asparagine to aspartic acid by controlling the forward primer and the reverse primer so as to form the isolated xylanase gene with mutations.

With continued reference to FIG. 1, the site-specific mutagenesis method in accordance with the preferred embodiment of the present invention is implemented by executing the first step "S1" of utilizing carriers to generate xylanase genes. In step "S1", the carriers are utilized to generate the xylanase genes to form the first recombinant plasmids for mass production of the xylanase genes; and the first recombinant plasmids are further transformed into the competent cells so as to form the wild-type expression carriers. A nucleotide sequence of the wild-type xylanase gene used herein has been registered in a nucleotide sequence database of GenBank database (accession number AY941119). The wild-type xylanase gene is separated from rumen microorganisms. A pET system for producing the carriers used herein is shown for exemplification and not by way of limitation. The pET system is operated as follows:

The wild-type xylanase gene is preserved in a plasmid so as to form a xylanase-gene-contained recombinant plasmid. Preferably, the plasmid is selected from pGEX5X-1 (Amersham Pharmacia, Sweden). The recombinant plasmids are transformed into first microorganisms which are inoculated in a cultivation liquid containing antibiotics. In a preferred embodiment, the first microorganism is selected from colon *bacillus* DH5 α (*E. coli* DH5α). In a preferred embodiment, the cultivation liquid is selected from Luria-Bertani broth cultivation liquid containing antibiotics. Preferably, the antibiotic is selected from ampicillin which has a concentration of 100 μg/mL. Next, the first microorganism is cultivated for 16 hours at 37 degrees Centigrade. Preferably, a plasmid purification kit (commercially available from mini-MTM plasmid DNA extraction system, Viogene, Taiwan) is utilized to process and purify the plasmids so as to generate purified recombinant plasmids. Subsequently, two restriction enzymes are utilized to cut the purified recombinant plasmids. Preferably, the two restriction enzymes are selected from BamHI and NotI. After cutting the first plasmids, a DNA ligase is utilized to react a DNA ligation for combining the xylanase-gene-contained DNA fragments with the broken first plasmids so as to form the first recombinant plasmids containing xylanase gene. Preferably, the first recombinant plasmids are selected from pET21C (Novagen, USA) and the DNA ligase is selected from a T4 ligase (Roche, Germany). In this circumstance, the operation of the pET system is completed. Subsequently, the first recombinant plasmids are transformed into the competent cells which are confirmed by DNA sequencing. Preferably, the competent cells are selected from colon *bacillus* DH5α. Accordingly, the first step "S1" is completely executed.

With continued reference to FIG. 1, the site-specific mutagenesis method in accordance with the preferred embodiment of the present invention is implemented by executing the second step "S2" of executing a polymerase chain reaction. In step "S2", the first recombinant plasmids are mixed with dNTP, reaction buffer, forward primer, reverse primer and polymerase for processing the polymerase chain reaction so as to form the second recombinant plasmids, and the second recombinant plasmids are further transformed into the competent cells so as to form the mutated-type expression carriers. In operation, the first recombinant plasmids, dNTP, reaction buffer, forward primer, reverse primer and polymerase are added in a 200 μL thin-wall centrifuge tube. Preferably, the amount of the first recombinant plasmid is 50 ng. The dNTP consists of dATP, dTTP, dCTP and dGTP, each of which preferably has a concentration of 360 μM. The reaction buffer is selected from 10× reaction buffer with an amount of 5 μL. The forward primer and reverse primer have a concentration of 300 nM. In a preferred embodiment, the forward primer has a nucleotide sequence selected from (SEQ ID NO:1) while the reverse primer has a nucleotide sequence selected from (SEQ ID NO:2), as best shown in TABLE 1. In TABLE 1, positions of the nucleotide sequences of the forward primer and reverse primer are underlined indicating that a mutation position of the nucleotide sequence. The polymerase is selected from 0.75 μL (3.75 units) of Expand long template DNA polymerase (Roche, Germany). Finally, distilled water is added to a total amount of 50 μL. After a short centrifugal operation, the polymerase is disposed in a Polymerase Chain Reaction (PCR) machine which is preferably selected from Applied Biosystems 2007 PCR system (USA).

TABLE 1

Genetic Sequence of Forward Primer and Reverse Primer

| | |
|---|---|
| forward primer SEQ ID NO:1 | 5'CTGGTTAGATGACACCGGTGGTAGC3' |
| reverse primer SEQ ID NO:2 | 5'GCTACCACCGGTGTCATCTAACCAG3' |

Turning now to FIG. 2, a schematic view of a nucleotide sequence (SEQ ID NO:3) of an isolated xylanase gene with mutations in accordance with a first embodiment of the present invention is illustrated. In the polymerase chain reaction, the xylanase gene is denatured in high temperature. Next, the forward primer or the reverse primer and the denatured single-strand xylanase gene are annealing such that the forward primer and the reverse primer correspondingly determine two predetermined points of the denatured xylanase gene between which to duplicate a DNA fragment. Subsequently, the polymerase can cause extensions of the forward primer and the reverse primer along the denatured single-strand xylanase genes to form the duplicated DNA fragment. In operation, the PCR machine is set at a temperature of 95 degrees Centigrade for 3 minutes, 95 degrees Centigrade for 45 seconds for denaturing, 55 degrees Centigrade for 1 minute for annealing, and 68 degrees Centigrade for 9 minutes for extension which is a cycle for polymerase chain reaction. The PCR machine repeatedly executes the cycle 20 times. Subsequently, the PCR machine is set at a temperature of 55 degrees Centigrade for 1 minute and 68 degrees Centigrade for 15 minutes and is dropped to 4 degrees Centigrade so as to obtain reaction products of the polymerase chain reaction. Consequently, the polymerase chain reaction is completed. The second recombinant plasmids containing an isolated xylanase gene with mutations are formed by the polymerase chain reaction.

Next, a restriction enzyme is added to 200 μL of the reaction product of the polymerase chain reaction so as to cut the unmutated first recombinant plasmids in the reaction product of the polymerase chain reaction. Preferably, the restriction enzyme is selected from 1 μL of DpnI reacting at a temperature of 37 degrees Centigrade for 1 hour, 65 degrees Centigrade for 10 minutes such that the second recombinant plasmids are transformed into the first microorganisms so as to form the mutated-type expression carriers. The mutated-type expression carriers are cultivated and sieved in the antibiotic-contained cultivation liquid. Finally, three transformed colonies are selected and the second recombinant plasmids are confirmed by sequencing. Accordingly, the first step "S2" is completely executed. Since each of the forward primer and the reverse primer has a mutation position, the reproduction of the xylanase genes in the polymerase chain reaction can generate the second recombinant plasmids containing the isolated xylanase gene with mutations. In this manner, the fifty-eighth amino of the xylanase gene is mutated from asparagine to aspartic acid so as to form the isolated xylanase gene with mutations. The isolated xylanase gene has the nucleotide sequence (SEQ ID NO:3) shown in FIG. 2. In FIG. 2, the fifty-eighth amino of the isolated xylanase gene as well as the aspartic acid is indicated in a frame.

The difference between the isolated xylanase gene with mutations in accordance with the present invention and the xylanase gene are verified. Each of the isolated xylanase gene with mutations in accordance with the present invention and the xylanase gene is utilized to produce a wild-type xylanase gene and a mutated-type xylanase gene for use in measuring reaction activity of the enzyme. In comparison with the wild-type xylanase gene, the isolated xylanase gene in accordance with the present invention can enhance the reaction activity of the enzyme.

Figure 3A:
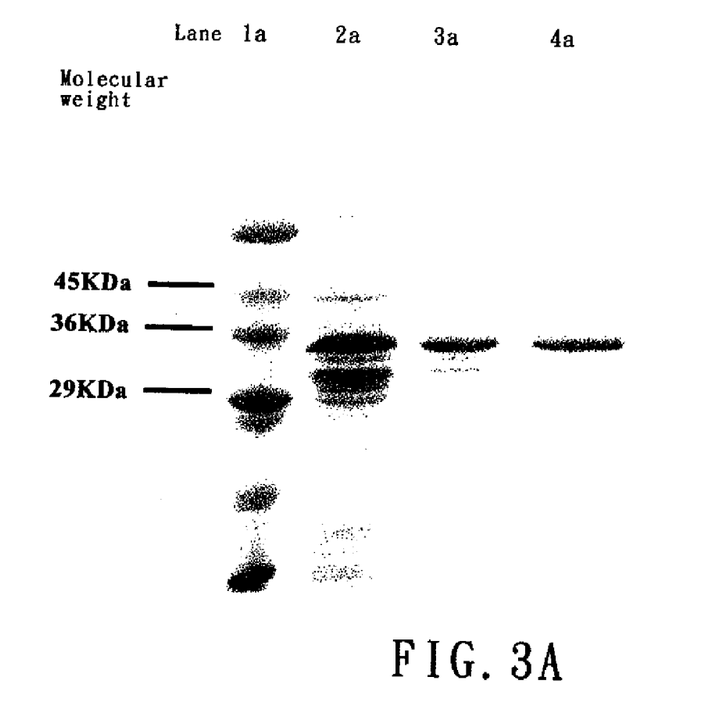
FIG. 3A is a SDS-PAGE analysis image of a wild-type xylanase gene in accordance with the first embodiment of the present invention.
Figure 3B:
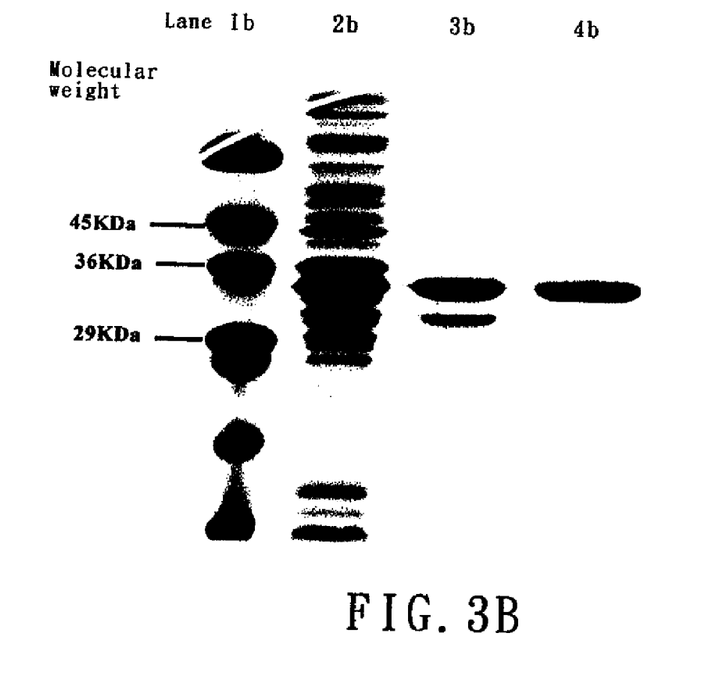
FIG. 3B is a SDS-PAGE analysis image of a mutated-type xylanase in accordance with the first embodiment of the present invention.

Turning now to FIG. 3A, a SDS-PAGE (sodium dodecyl sulfate-polyacrylamide gel electrophotesis) analysis image of a wild-type xylanase gene in accordance with the first embodiment of the present invention is illustrated. Turning to FIG. 3B, a SDS-PAGE analysis image of a mutated-type xylanase gene in accordance with the first embodiment of the present invention is illustrated. Firstly, the first recombinant plasmids are extracted from the wild-type expression carriers and are transformed into second microorganisms so as to form growth carriers that contain the xylanase gene. Preferably, the second microorganism is selected from colon bacillus BL21 (DE3). The growth carriers are inoculated in 5 mL of an antibiotic-contained cultivation liquid to produce a bacteria liquid which is cultivated for 16 hours at 37 degrees Centigrade and is vibrated at 255 rpm by a shaker. After completely cultivating the cultivation liquid, 5 mL of the bacteria liquid is further inoculated in 500 mL of the antibiotic-contained cultivation liquid which is cultivated at 37 degrees Centigrade and is vibrated at 180 rpm by a shaker. When a value of OD600 of the bacteria liquid is 0.6-0.8, a medium of IPTG (isopropyl-β-D-thiogalactoside) is added as a revulsive. Preferably, the IPTG has a final concentration of 1 mM. The wild-type xylanase is generated after the revulsion of IPTG for 4 hours. Subsequently, 4,000 g of the bacteria liquid is processed for 20 minutes to precipitate bacteria by a centrifuge. The bacteria are dissolved in a citric acid buffer. Preferably, the citric acid buffer has a pH value of 6 and a concentration of 50 mM. Subsequently, phenylmethylsulfonyl fluoride (PMSF) and leupeptin are added in the bacteria liquid as a protease inhibitor so as to avoid the protease in the second microorganisms dissolving the wild-type xylanase. Preferably, the PMSF has a final concentration of 0.5 mM and the leupeptin has a final concentration of 1 μg/mL. The bacteria are broken ultrasonically to obtain a crude enzyme liquid. 10,000 g of the crude enzyme liquid is processed and is separated for 30 minutes by a centrifuge. Furthermore, the crude enzyme liquid is purified in a CM-Sepharose column and Ni-NTA affinity column for purification so as to obtain the purified wild-type xylanase. Finally, the purified wild-type xylanase is dialyzed to remove redundant salts and to replace the citric acid buffer. Accordingly, the purified wild-type xylanase is prepared and can be applied in the following measuring procedure.

A manufacturing method for the mutated-type xylanase is identical with that for the wild-type xylanase which is incorporated herein by reference. The extraction of the first recombinant plasmids from the wild-type expression carriers is only changed to the extraction of the second recombinant plasmids from the mutated-type xylanase. However, the detailed descriptions for the extractions of the second recombinant plasmids from the mutated-type xylanase are omitted for the sake of simplicity. Accordingly, the mutated-type xylanase is prepared and can be applied in the following measuring procedure.

With continued reference to FIGS. 3A and 3B, the wild-type xylanase and the mutated-type xylanase are further analyzed by SDS-PAGE to identify their purification statuses and molecular weight. In FIGS. 3A and 3B, columns 1a and 1b represent a mark of molecular weight for standard protein; column 2a represents a crude enzyme liquid formed from the first recombinant plasmids; column 3a represents the wild-type xylanase purified in the CM-Sepharose column; column 4a represents the wild-type xylanase purified in the Ni-NTA affinity column; column 2b represents a crude enzyme liquid formed from the first recombinant plasmids; column 3b represents the mutated-type xylanase purified in the CM-Sepharose column; and column 4b represents the mutated-type xylanase purified in the Ni-NTA affinity column. As indicated in FIGS. 3A and 3B, the molecular weights of the wild-type xylanase and the mutated-type xylanase are approximately 34 KDa.

In TABLE 2, enzyme activities of the wild-type xylanase and the mutated-type xylanase are measured in various purification stages and are compared. Firstly, 5 ng of the wild-type xylanase is added to a substrate.

Preferably, the substrate is selected from a liquid buffer containing 20 mg/mL of soluable oat spelt xylan. The liquid buffer is selected from 50 mM of citric acid buffer which has a pH value of 6.5. After mixing, the wild-type xylanase buffer is reacted at the temperature of 50 degrees Centigrade for 10 minutes such that the xylanase can decompose the xylan contained in the substrate. Subsequently, a method of DNS (dinitrosalicylic acid) is utilized to process quantitative reduction for the redundant of the xylan remained in the substrate so as to obtain indexes of enzyme activities (U/mg). A unit activity (U) is the substrate activity of catalyzing 1 μmole per minute. Preferably, a BCA protein quantitative set (available from Pierce Ltd., USA) can be utilized to quantitate the concentration of the wild-type xylanase.

A measuring method for the activity of mutated-type xylanase is identical with that for the wild-type xylanase which is incorporated herein by reference. Hence, the detailed descriptions for the measuring method for the activity of mutated-type xylanase are omitted for the sake of simplicity. The enzyme activity of mutated-type xylanase is 2.4 times that of the wild-type xylanase, as indicated in TABLE 2. Advantageously, the xylanase gene in accordance with the present invention increases its reaction activity.

TABLE 2

Enzyme Aactivities of Wild-Type Xylanase and Mutated-Type Xylanase

| purification stage | enzyme activity of wild-type xylanase (U/mg) | enzyme activity of mutated-type xylanase |
|---|---|---|
| Crude enzyme liquid | 2,568.27 | 11,264.39 |
| CM-Sepharose column | 14,568.65 | 45,396.16 |
| Ni-NTA affinity column | 23,244.85 | 57,496.61 |

Figure 4:
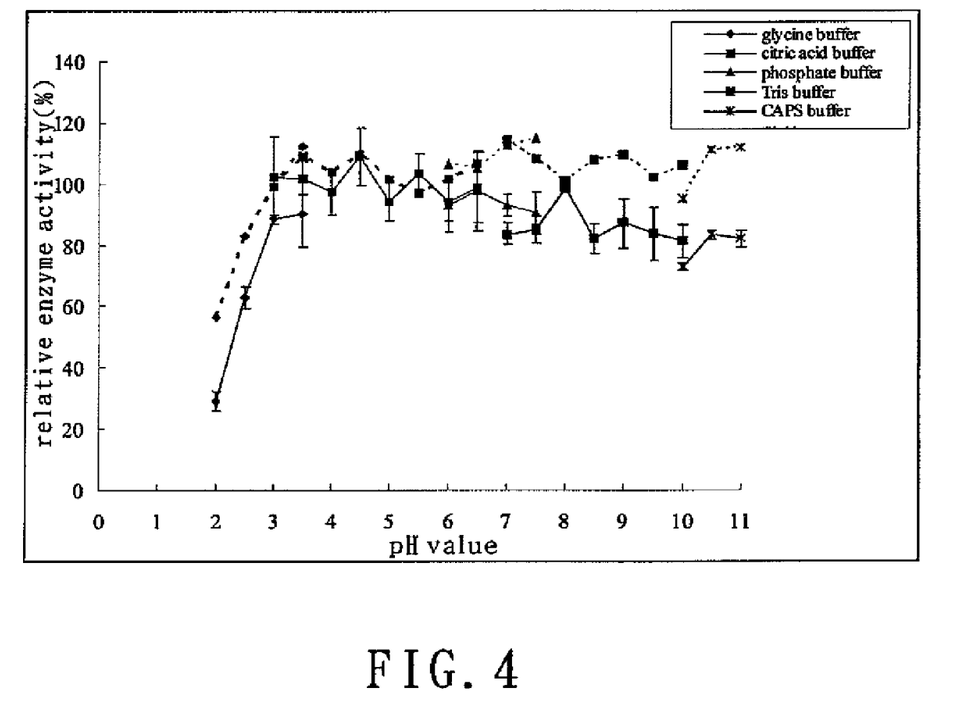
FIG. 4 is a chart illustrating relative enzyme activities of the wild-type xylanase and the mutated-type xylanase in accordance with the first embodiment of the present invention in relation to pH values.

Turning now to FIG. 4, a chart illustrating relative enzyme activities of the wild-type xylanase and the mutated-type xylanase in relation to pH values is shown. In order to demonstrate the relative enzyme activities of the wild-type xylanase and the mutated-type xylanase in various pH values, an enzyme pH optimal reaction test for the wild-type xylanase and the mutated-type xylanase is processed. 5 ng of the wild-type xylanase is added to 295 μg of substrate which is selected from a liquid buffer containing 20 mg/mL of soluable oat spelt xylan. In an example, the liquid buffer is selected from glycine buffer which has a range of pH value from 2.0 to 3.5. In another example, the liquid buffer is selected from citric acid buffer which has a range of pH value from 3.0 to 6.5. In another example, the liquid buffer is selected from phosphate buffer which has a range of pH value from 6.0 to 7.5. In another example, the liquid buffer is selected from Tris buffer which has a range of pH value from 7.0 to 10.0. In another example, the liquid buffer is selected from CAPS buffer which has a range of pH value from 10.0 to 11.0. After mixing, the wild-type xylanase buffer is reacted at an appropriate temperature for 10 minutes such that the xylanase can decompose the xylan contained in the substrate. Subsequently, the method of DNS (dinitrosalicylic acid) is utilized to process quantitative reduction for the redundant of the xylan remained in the substrate so as to estimate indexes of enzyme activities. The enzyme pH optimal reaction test is operated at a pH standard of 6.5 so as to further estimate other pH values of the enzyme activities.

With continued reference to FIG. 4, the operation for measuring the activity of mutated-type xylanase is identical with that for the wild-type xylanase which is incorporated herein by reference. Hence, the detailed descriptions for the operation for measuring the activity of mutated-type xylanase are omitted for the sake of simplicity. However, it appears that the mutated-type xylanase in accordance with the present invention has a greater reaction activity in the acid or base environment than that of the wild-type xylanase. Accordingly, the mutated-type xylanase in accordance with the present invention enhances its reaction activity.

Figure 5:
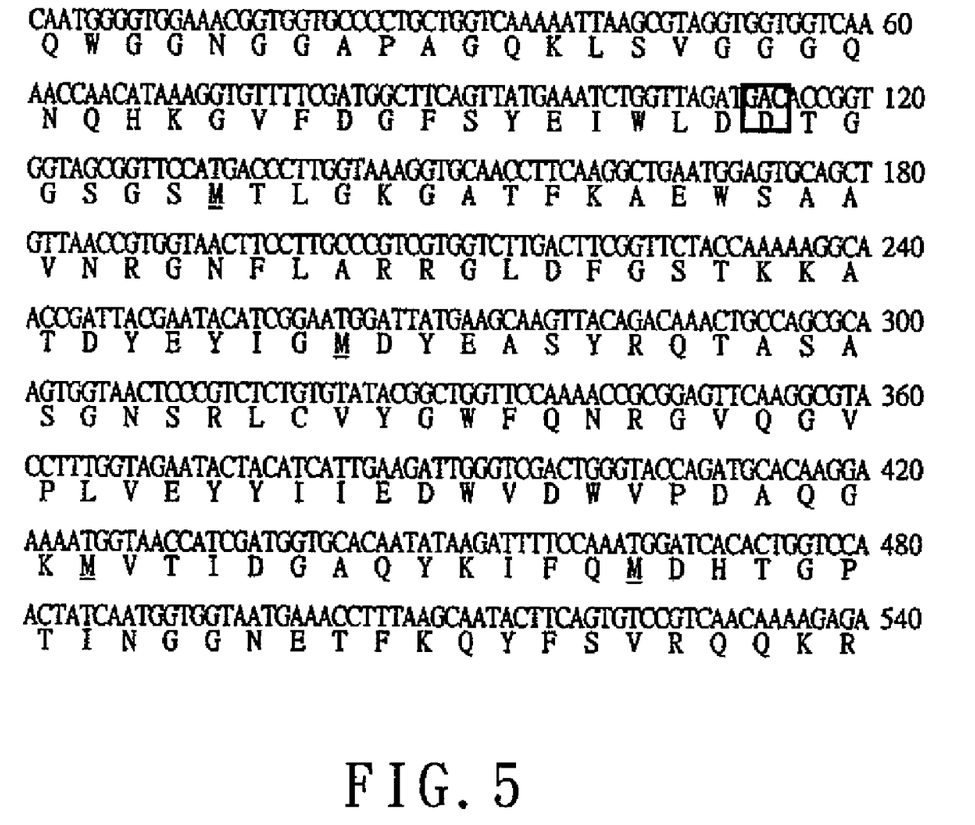
FIG. 5 is a schematic view illustrating a nucleotide sequence (SEQ ID NO:4) of an isolated xylanase gene with mutations in accordance with a second embodiment of the present invention.

Turning now to FIG. 5, a schematic view of a nucleotide sequence (SEQ ID NO:4) of an isolated xylanase gene with mutations in accordance with a second embodiment of the present invention is illustrated. The isolated xylanase gene has the nucleotide sequence (SEQ ID NO:4) shown in FIG. 6. In FIG. 6, encoding a mutation position of the thirty-eighth amino of the isolated xylanase gene as well as the aspartic acid is indicated in a frame. The SEQ ID NO:4 is a nucleotide sequence from 21st to 100 amino of the SEQ ID NO:3. Although the mutation positions of the SEQ ID NOS:3 and 4 are different, the amino positions of the SEQ ID NOS:3 and 4 are substantially the same. Advantageously, it appears that the mutated-type xylanase and the site-specific mutagenesis method thereof in accordance with the second embodiment of the present invention are successful in enhancing its reaction activity of the enzyme.

As has been previously described, the site-specific mutagenesis method in accordance with the present invention is utilized to mutate a fifty-eighth amino acid or a thirty-eighth amino acid of an enzyme gene from asparagine to aspartic acid so as to form the enzyme gene with mutations. Preferably, the enzyme is selected from oxidoreductases, transferase, hydrolase, lipase, isomerase or synthase. Preferably, the hydrolase is selected from the xylanase.

In addition to this, the isolated xylanase gene with mutations in accordance with the present invention can be further utilized and incorporated into a plasmid or a chromosome by recombinant DNA technology. In another embodiment, the isolated xylanase gene in accordance with the present invention can be incorporated into a cell by a genetic engineering process.

As has been discussed above, the conventional xylanases possess a lower degree of reaction activity such that a greater amount of the xylanases must be used. Conversely, the site-specific mutagenesis method in accordance with the present invention is processed to mutate at least one amino acid of the xylanase gene from asparagine to aspartic acid so as to form the isolated xylanase gene with mutations. Advantageously, the isolated xylanase gene and the site-specific mutagenesis method in accordance with the present invention are successful in enhancing high reaction activity of the xylanase.

Although the invention has been described in detail with reference to its presently preferred embodiments, it will be understood by one of ordinary skill in the art that various modifications can be made without departing from the spirit and the scope of the invention, as set forth in the appended claims.

What is claimed is:

1. An isolated xylanase gene with mutations, comprising: a nucleotide sequence encoding a xylanase having the amino acid sequence of SEQ ID NO:3.

* * * * *

SEQUENCE LISTING

<160> NUMBER OF SEQ ID NOS: 6

<210> SEQ ID NO 1
<211> LENGTH: 25
<212> TYPE: DNA
<213> ORGANISM: artificial sequence
<220> FEATURE:
<223> OTHER INFORMATION: Synthetic Oligonucleotide Primer

<400> SEQUENCE: 1
ctggttagat gacaccggtg gtagc                                          25

<210> SEQ ID NO 2
<211> LENGTH: 25
<212> TYPE: DNA
<213> ORGANISM: artificial sequence
<220> FEATURE:
<223> OTHER INFORMATION: Synthetic Oligonucleotide Primer

<400> SEQUENCE: 2
gctaccaccg gtgtcatcta accag                                          25

<210> SEQ ID NO 3
<211> LENGTH: 969
<212> TYPE: DNA
<213> ORGANISM: unknown
<220> FEATURE:
<223> OTHER INFORMATION: Attempts have been made to determine the genus
      species, but it remains unknown at this time.

<400> SEQUENCE: 3

```
atg gct agc atg act ggt gga cag caa atg ggt cgg atc ccg tta act      48
Met Ala Ser Met Thr Gly Gly Gln Gln Met Gly Arg Ile Pro Leu Thr
 1               5                  10                  15 gtt gct aag gcc caa tgg ggt gga aac ggt ggt gcc cct gct ggt caa      96
Val Ala Lys Ala Gln Trp Gly Gly Asn Gly Gly Ala Pro Ala Gly Gln
             20                  25                  30 aaa tta agc gta ggt ggt ggt caa aac caa cat aaa ggt gtt ttc gat     144
Lys Leu Ser Val Gly Gly Gly Gln Asn Gln His Lys Gly Val Phe Asp
         35                  40                  45 ggc ttc agt tat gaa atc tgg tta gat gac acc ggt ggt agc ggt tcc     192
Gly Phe Ser Tyr Glu Ile Trp Leu Asp Asp Thr Gly Gly Ser Gly Ser
     50                  55                  60 atg acc ctt ggt aaa ggt gca acc ttc aag gct gaa tgg agt gca gct     240
Met Thr Leu Gly Lys Gly Ala Thr Phe Lys Ala Glu Trp Ser Ala Ala
 65                  70                  75                  80 gtt aac cgt ggt aac ttc ctt gcc cgt cgt ggt ctt gac ttc ggt tct     288
Val Asn Arg Gly Asn Phe Leu Ala Arg Arg Gly Leu Asp Phe Gly Ser
                 85                  90                  95 acc aaa aag gca acc gat tac gaa tac atc gga atg gat tat gaa gca     336
Thr Lys Lys Ala Thr Asp Tyr Glu Tyr Ile Gly Met Asp Tyr Glu Ala
            100                 105                 110 agt tac aga caa act gcc agc gca agt ggt aac tcc cgt ctc tgt gta     384
Ser Tyr Arg Gln Thr Ala Ser Ala Ser Gly Asn Ser Arg Leu Cys Val
        115                 120                 125 tac ggc tgg ttc caa aac cgc gga gtt caa ggc gta cct ttg gta gaa     432
Tyr Gly Trp Phe Gln Asn Arg Gly Val Gln Gly Val Pro Leu Val Glu
    130                 135                 140 tac tac atc att gaa gat tgg gtc gac tgg gta cca gat gca caa gga     480
Tyr Tyr Ile Ile Glu Asp Trp Val Asp Trp Val Pro Asp Ala Gln Gly
145                 150                 155                 160
```

-continued

```
aaa atg gta acc atc gat ggt gca caa tat aag att ttc caa atg gat      528
Lys Met Val Thr Ile Asp Gly Ala Gln Tyr Lys Ile Phe Gln Met Asp
                165                 170                 175 cac act ggt cca act atc aat ggt ggt aat gaa acc ttt aag caa tac      576
His Thr Gly Pro Thr Ile Asn Gly Gly Asn Glu Thr Phe Lys Gln Tyr
            180                 185                 190 ttc agt gtc cgt caa caa aag aga act tct ggt cat att act gta tca      624
Phe Ser Val Arg Gln Gln Lys Arg Thr Ser Gly His Ile Thr Val Ser
        195                 200                 205 gat cac ttt aag gca tgg gcc agt caa ggt tgg ggt att gga aac ctc      672
Asp His Phe Lys Ala Trp Ala Ser Gln Gly Trp Gly Ile Gly Asn Leu
    210                 215                 220 tat gaa gtt gca ttg aac gca gaa ggt tgg caa agt agt ggt gtc gct      720
Tyr Glu Val Ala Leu Asn Ala Glu Gly Trp Gln Ser Ser Gly Val Ala
225                 230                 235                 240 gac gtc acc aag ttg gat gtc tac acc acc aaa caa ggt tct gct cct      768
Asp Val Thr Lys Leu Asp Val His Thr Thr Lys Gln Gly Ser Ala Pro
                245                 250                 255 cgt act acc acc act acc cgt act act acc cgt act act aca aga          816
Arg Thr Thr Thr Thr Thr Arg Thr Thr Thr Arg Thr Thr Thr Arg
            260                 265                 270 aca ctt cca acc act ggc aat aag tgt tct gcc aag att act gcc caa      864
Thr Leu Pro Thr Thr Gly Asn Lys Cys Ser Ala Lys Ile Thr Ala Gln
        275                 280                 285 ggt tac aag tgt tgt agt gat cca aat tgt gtt att tac tac act gat      912
Gly Tyr Lys Cys Cys Ser Asp Pro Asn Cys Val Ile Tyr Tyr Thr Asp
    290                 295                 300 gac gat ggt aaa tgg ggt aaa gcg gcc gca ctc gag cac cac cac cac      960
Asp Asp Gly Lys Trp Gly Lys Ala Ala Ala Leu Glu His His His His
305                 310                 315                 320 cac cac tga                                                          969
His His
```

<210> SEQ ID NO 4
<211> LENGTH: 540
<212> TYPE: DNA
<213> ORGANISM: unknown
<220> FEATURE:
<223> OTHER INFORMATION: Attempts have been made to determine the genus
      species, but it remains unknown at this time.

<400> SEQUENCE: 4

```
caa tgg ggt gga aac ggt ggt gcc cct gct ggt caa aaa tta agc gta       48
Gln Trp Gly Gly Asn Gly Gly Ala Pro Ala Gly Gln Lys Leu Ser Val
1               5                   10                  15 ggt ggt ggt caa aac caa cat aaa ggt gtt ttc gat ggc ttc agt tat       96
Gly Gly Gly Gln Asn Gln His Lys Gly Val Phe Asp Gly Phe Ser Tyr
            20                  25                  30 gaa atc tgg tta gat gac acc ggt ggt agc ggt tcc atg acc ctt ggt      144
Glu Ile Trp Leu Asp Asp Thr Gly Gly Ser Gly Ser Met Thr Leu Gly
        35                  40                  45 aaa ggt gca acc ttc aag gct gaa tgg agt gca gct gtt aac cgt ggt      192
Lys Gly Ala Thr Phe Lys Ala Glu Trp Ser Ala Ala Val Asn Arg Gly
    50                  55                  60 aac ttc ctt gcc cgt cgt ggt ctt gac ttc ggt tct acc aaa aag gca      240
Asn Phe Leu Ala Arg Arg Gly Leu Asp Phe Gly Ser Thr Lys Lys Ala
65                  70                  75                  80 acc gat tac gaa tac atc gga atg gat tat gaa gca agt tac aga caa      288
Thr Asp Tyr Glu Tyr Ile Gly Met Asp Tyr Glu Ala Ser Tyr Arg Gln
                85                  90                  95 act gcc agc gca agt ggt aac tcc cgt ctc tgt gta tac ggc tgg ttc      336
```

-continued

```
             Thr Ala Ser Ala Ser Gly Asn Ser Arg Leu Cys Val Tyr Gly Trp Phe
                     100                 105                 110 caa aac cgc gga gtt caa ggc gta cct ttg gta gaa tac tac atc att       384
Gln Asn Arg Gly Val Gln Gly Val Pro Leu Val Glu Tyr Tyr Ile Ile
        115                 120                 125 gaa gat tgg gtc gac tgg gta cca gat gca caa gga aaa atg gta acc       432
Glu Asp Trp Val Asp Trp Val Pro Asp Ala Gln Gly Lys Met Val Thr
130                 135                 140 atc gat ggt gca caa tat aag att ttc caa atg gat cac act ggt cca       480
Ile Asp Gly Ala Gln Tyr Lys Ile Phe Gln Met Asp His Thr Gly Pro
145                 150                 155                 160 act atc aat ggt ggt aat gaa acc ttt aag caa tac ttc agt gtc cgt       528
Thr Ile Asn Gly Gly Asn Glu Thr Phe Lys Gln Tyr Phe Ser Val Arg
                165                 170                 175 caa caa aag aga                                                        540
Gln Gln Lys Arg
180
```

<210> SEQ ID NO 5
<211> LENGTH: 322
<212> TYPE: PRT
<213> ORGANISM: unknown
<220> FEATURE:
<223> OTHER INFORMATION: Attempts have been made to determine the genus
      species, but it remains unknown at this time.

<400> SEQUENCE: 5

```
Met Ala Ser Met Thr Gly Gly Gln Gln Met Gly Arg Ile Pro Leu Thr
1               5                   10                  15

Val Ala Lys Ala Gln Trp Gly Gly Asn Gly Gly Ala Pro Ala Gly Gln
            20                  25                  30

Lys Leu Ser Val Gly Gly Gln Asn Gln His Lys Gly Val Phe Asp
        35                  40                  45

Gly Phe Ser Tyr Glu Ile Trp Leu Asp Asp Thr Gly Gly Ser Gly Ser
    50                  55                  60

Met Thr Leu Gly Lys Gly Ala Thr Phe Lys Ala Glu Trp Ser Ala Ala
65                  70                  75                  80

Val Asn Arg Gly Asn Phe Leu Ala Arg Arg Gly Leu Asp Phe Gly Ser
                85                  90                  95

Thr Lys Lys Ala Thr Asp Tyr Glu Tyr Ile Gly Met Asp Tyr Glu Ala
            100                 105                 110

Ser Tyr Arg Gln Thr Ala Ser Ala Ser Gly Asn Ser Arg Leu Cys Val
        115                 120                 125

Tyr Gly Trp Phe Gln Asn Arg Gly Val Gln Gly Val Pro Leu Val Glu
    130                 135                 140

Tyr Tyr Ile Ile Glu Asp Trp Val Asp Trp Val Pro Asp Ala Gln Gly
145                 150                 155                 160

Lys Met Val Thr Ile Asp Gly Ala Gln Tyr Lys Ile Phe Gln Met Asp
                165                 170                 175

His Thr Gly Pro Thr Ile Asn Gly Gly Asn Glu Thr Phe Lys Gln Tyr
            180                 185                 190

Phe Ser Val Arg Gln Gln Lys Arg Thr Ser Gly His Ile Thr Val Ser
        195                 200                 205

Asp His Phe Lys Ala Trp Ala Ser Gln Gly Trp Gly Ile Gly Asn Leu
    210                 215                 220

Tyr Glu Val Ala Leu Asn Ala Glu Gly Trp Gln Ser Ser Gly Val Ala
225                 230                 235                 240
```

-continued

```
Asp Val Thr Lys Leu Asp Val His Thr Thr Lys Gln Gly Ser Ala Pro
            245                 250                 255

Arg Thr Thr Thr Thr Thr Arg Thr Thr Arg Thr Thr Thr Arg
            260                 265                 270

Thr Leu Pro Thr Thr Gly Asn Lys Cys Ser Ala Lys Ile Thr Ala Gln
            275                 280                 285

Gly Tyr Lys Cys Cys Ser Asp Pro Asn Cys Val Ile Tyr Tyr Thr Asp
        290                 295                 300

Asp Asp Gly Lys Trp Gly Lys Ala Ala Ala Leu Glu His His His His
305                 310                 315                 320

His His

<210> SEQ ID NO 6
<211> LENGTH: 180
<212> TYPE: PRT
<213> ORGANISM: unknown
<220> FEATURE:
<223> OTHER INFORMATION: Attempts have been made to determine the genus
      species, but it remains unknown at this time.

<400> SEQUENCE: 6

Gln Trp Gly Gly Asn Gly Gly Ala Pro Ala Gly Gln Lys Leu Ser Val
 1               5                  10                  15

Gly Gly Gly Gln Asn Gln His Lys Gly Val Phe Asp Gly Phe Ser Tyr
            20                  25                  30

Glu Ile Trp Leu Asp Asp Thr Gly Gly Ser Gly Ser Met Thr Leu Gly
            35                  40                  45

Lys Gly Ala Thr Phe Lys Ala Glu Trp Ser Ala Ala Val Asn Arg Gly
     50                  55                  60

Asn Phe Leu Ala Arg Arg Gly Leu Asp Phe Gly Ser Thr Lys Lys Ala
 65                  70                  75                  80

Thr Asp Tyr Glu Tyr Ile Gly Met Asp Tyr Glu Ala Ser Tyr Arg Gln
                85                  90                  95

Thr Ala Ser Ala Ser Gly Asn Ser Arg Leu Cys Val Tyr Gly Trp Phe
            100                 105                 110

Gln Asn Arg Gly Val Gln Gly Val Pro Leu Val Glu Tyr Tyr Ile Ile
            115                 120                 125

Glu Asp Trp Val Asp Trp Val Pro Asp Ala Gln Gly Lys Met Val Thr
            130                 135                 140

Ile Asp Gly Ala Gln Tyr Lys Ile Phe Gln Met Asp His Thr Gly Pro
145                 150                 155                 160

Thr Ile Asn Gly Gly Asn Glu Thr Phe Lys Gln Tyr Phe Ser Val Arg
                165                 170                 175

Gln Gln Lys Arg
            180
```